(12) United States Patent
Schulz et al.

(10) Patent No.: US 8,887,726 B2
(45) Date of Patent: Nov. 18, 2014

(54) RESPIRATORY MASK

(75) Inventors: Gerd Schulz, Schenefeld (DE); Martin Eifler, Glückstadt (DE)

(73) Assignee: Weinmann Gerate fur Medizin GmbH & Co. KG, Hamburg (DE)

( * ) Notice: Subject to any disclaimer, the term of this patent is extended or adjusted under 35 U.S.C. 154(b) by 2157 days.

(21) Appl. No.: 11/883,822

(22) PCT Filed: Sep. 1, 2005

(86) PCT No.: PCT/DE2005/001535
§ 371 (c)(1),
(2), (4) Date: Sep. 24, 2007

(87) PCT Pub. No.: WO2006/024288
PCT Pub. Date: Mar. 9, 2006

(65) Prior Publication Data
US 2008/0210241 A1    Sep. 4, 2008

(30) Foreign Application Priority Data

Sep. 3, 2004 (DE) .......................... 10 2004 043 208

(51) Int. Cl.
*A61M 16/06* (2006.01)
*A62B 18/02* (2006.01)
*A61M 16/08* (2006.01)

(52) U.S. Cl.
CPC ........... *A61M 16/06* (2013.01); *A61M 16/0638* (2013.01); *A61M 2205/6045* (2013.01); *A61M 16/0825* (2013.01)
USPC .................................. 128/206.21; 128/205.25

(58) Field of Classification Search
CPC . A61M 16/06; A61M 16/0825; A61M 16/20; A61M 16/208; A61M 16/209; A62B 18/02; A62B 18/025; A62B 18/06; A62B 18/10
USPC ............ 128/200.24, 202.27, 204.18, 205.25, 128/206.12, 206.18, 206.21–207.14
See application file for complete search history.

(56) References Cited

U.S. PATENT DOCUMENTS

| 3,824,999 | A | * | 7/1974 | King ......................... 128/207.17 |
| 5,765,553 | A |   | 6/1998 | Richards et al. |
| 5,921,239 | A | * | 7/1999 | McCall et al. ........... 128/205.25 |
| 5,924,420 | A | * | 7/1999 | Reischel et al. ......... 128/206.21 |

(Continued)

FOREIGN PATENT DOCUMENTS

| DE | 297 23 101 | 7/1998 |
| DE | 298 10 846 | 10/1998 |

(Continued)

*Primary Examiner* — Valerie L Skorupa
(74) *Attorney, Agent, or Firm* — Abel Law Group, LLP

(57) ABSTRACT

The invention relates to a respiratory mask comprising a mask body and an articulated connection piece that can be connected to a respiratory tube. On the mask body, at least one exhalation gap is located in the vicinity of a connection that holds the articulated connection piece. Preferably, the exhalation gap terminates in an umbrella-shaped outflow channel that runs away from the patient. Preferably, at least two components of the respiratory mask are interconnected without play.

3 Claims, 13 Drawing Sheets

(56) References Cited

U.S. PATENT DOCUMENTS

| | | | |
|---|---|---|---|
| 6,142,342 A * | 11/2000 | Lewis | 222/180 |
| 6,823,869 B2 * | 11/2004 | Raje et al. | 128/206.24 |
| 7,089,939 B2 * | 8/2006 | Walker et al. | 128/205.24 |
| 7,216,647 B2 | 5/2007 | Lang et al. | |
| 7,856,980 B2 | 12/2010 | Lang et al. | |
| 2003/0075180 A1 | 4/2003 | Raje et al. | |
| 2004/0045550 A1 * | 3/2004 | Lang et al. | 128/205.25 |
| 2004/0112384 A1 | 6/2004 | Lithgow et al. | |
| 2005/0076913 A1 * | 4/2005 | Ho et al. | 128/206.27 |
| 2005/0126567 A1 * | 6/2005 | Lurie | 128/203.11 |
| 2007/0157934 A1 | 7/2007 | Lang et al. | |
| 2011/0056498 A1 | 3/2011 | Lang et al. | |

FOREIGN PATENT DOCUMENTS

| | | |
|---|---|---|
| DE | 198 22 308 | 11/1999 |
| DE | 299 23 126 | 5/2000 |
| DE | 199 81 084 | 1/2002 |
| DE | 100 57 883 | 8/2002 |
| DE | 198 17 332 | 11/2002 |
| DE | 102004002125 | 8/2005 |
| DE | 102004002870 | 8/2005 |
| EP | 1314446 A2 | 5/2003 |
| WO | 2004022145 A1 | 3/2004 |

* cited by examiner

RESPIRATORY MASK

The invention concerns a respiratory mask with a mask body and an articulated connector that can be connected with a respiratory hose.

Respiratory masks are used, for example, in connection with ventilators to carry respiratory gas to the patient and to help carry away exhaled respiratory gas. The respiratory mask is typically connected with the ventilator by the respiratory hose.

A disadvantage of previously known respiratory masks is that the exhalation of the patient through the mask body and the respiratory hose causes an acoustic effect that is unpleasant for the patient and persons in the vicinity. In addition, the exhaled stream of air produces a cool draft that brushes along the patient's skin.

The objective of the present invention is to create a comfortable design of a respiratory mask that largely eliminates these unpleasant effects on the patient by the exhaled air.

In accordance with the invention, the solution to this problem is characterized by the fact that at least one exhalation gap is located in the vicinity of the mask body, preferably in the vicinity of a connection on the mask body that receives the articulated connector.

The respiratory mask of the invention, which is to be understood not only as a single part but rather as an element of a complete ventilator, comprises a mask body and an articulated connector that can be connected with a respiratory hose, such that at least one exhalation gap is located in the vicinity of the transition between the articulated connector and a connection on the mask body that receives the articulated connector. In particular, the arrangement of the exhalation gap between the mask body and the connector keeps the noise level low compared to other positions in which it could be arranged. In this position of the exhalation gap, $CO_2$ is also washed out especially effectively. Moreover, it is precisely in the area of transition between the mask body and the connector that it is possible to provide a large gap length, which is acoustically especially advantageous compared, for example, to holes and short slots.

The one or more exhalation gaps are preferably bounded by two outflow surfaces each.

The articulated connector is advantageously designed as a ball-and-socket joint and is supported on individual points, especially on two points, in a ball cage of the receiving connection. In this way, there is a slight amount of bearing friction, and easy mobility of the attached respiratory hose is guaranteed. Tolerances can also be compensated in a simple way.

In another advantageous embodiment of the respiratory mask, the one or more respiratory gaps are bounded by the outflow surfaces, such that they are located adjacent to at least one spacing element and in this regard are play-free or can even be provided with pretensioning relative to each other. This prevents the occurrence of undesired vibrations and resonances due to escaping air when play is present, for especially in an exhalation gap in a ball-and-socket joint, a large gap length is obtained. Under certain circumstances, this could prove acoustically unfavorable if moving parts are present in the gap.

In addition, the exhalation gap between two outflow surfaces can be produced largely tolerance-free if the surfaces forming the gap are pressed against each other by a pretensioning force, thus eliminating any play between them, and the height of the gap is adjusted by spacing elements between the surfaces. In a design of this type, the height of the gap depends, apart from the shape and positional tolerances of the surfaces that form the gap, only on the tolerance of the height of a rib used as a spacing element. Since typical rib heights in exhalation gaps are 0.1-0.5 mm, gap tolerances of ±0.005 mm or less can be produced with a high degree of process reliability. Consequently, flow and sound emissions can be maintained within very narrow limits.

The mask body and the connector are preferably joined with a mechanical coding system. This has the advantage of preventing incorrect attachment of the mask body and connector to each other and of preventing an incorrect combination of a connector with a mask body.

It is advantageous for the body of the mask and the connector to be attached to each other by a retaining ring with a locking device, for example, a bayonet catch. The retaining ring also serves to fix the exhalation gaps, for example, by pretensioning the outflow surfaces of the respiratory mask and complementary outflow surfaces on the retaining ring against each other.

In another advantageous embodiment of the respiratory mask, the outflow surfaces form an outflow channel, which carries away the respiratory gas flow at an angle of 10-45°, especially 20-30°, and especially preferably about 25° to a plane arranged frontally with respect to the face of the patient. In this way, the exhaled air is carried away from the patient in a basically umbrella-shaped path and is not unpleasantly perceived by the patient.

In addition, the outflow channel can be designed in such a way that it prevents the flow of exhaled air from moving in the general direction of the patient's eyes, since a draft of air towards the eyes is felt as especially unpleasant.

Furthermore, the respiratory mask can be designed in such a way that surfaces of the mask that bound the outflow channel are made of hard plastic, and surfaces of elements of the respiratory mask that are handled are made of soft plastic. In this way, on the one hand, the flow of respiratory gas is reliably carried away, and, on the other hand, the ease of handling and operating the respiratory mask is improved.

The invention is explained below with reference to the examples illustrated in the figures.

Figure 1:
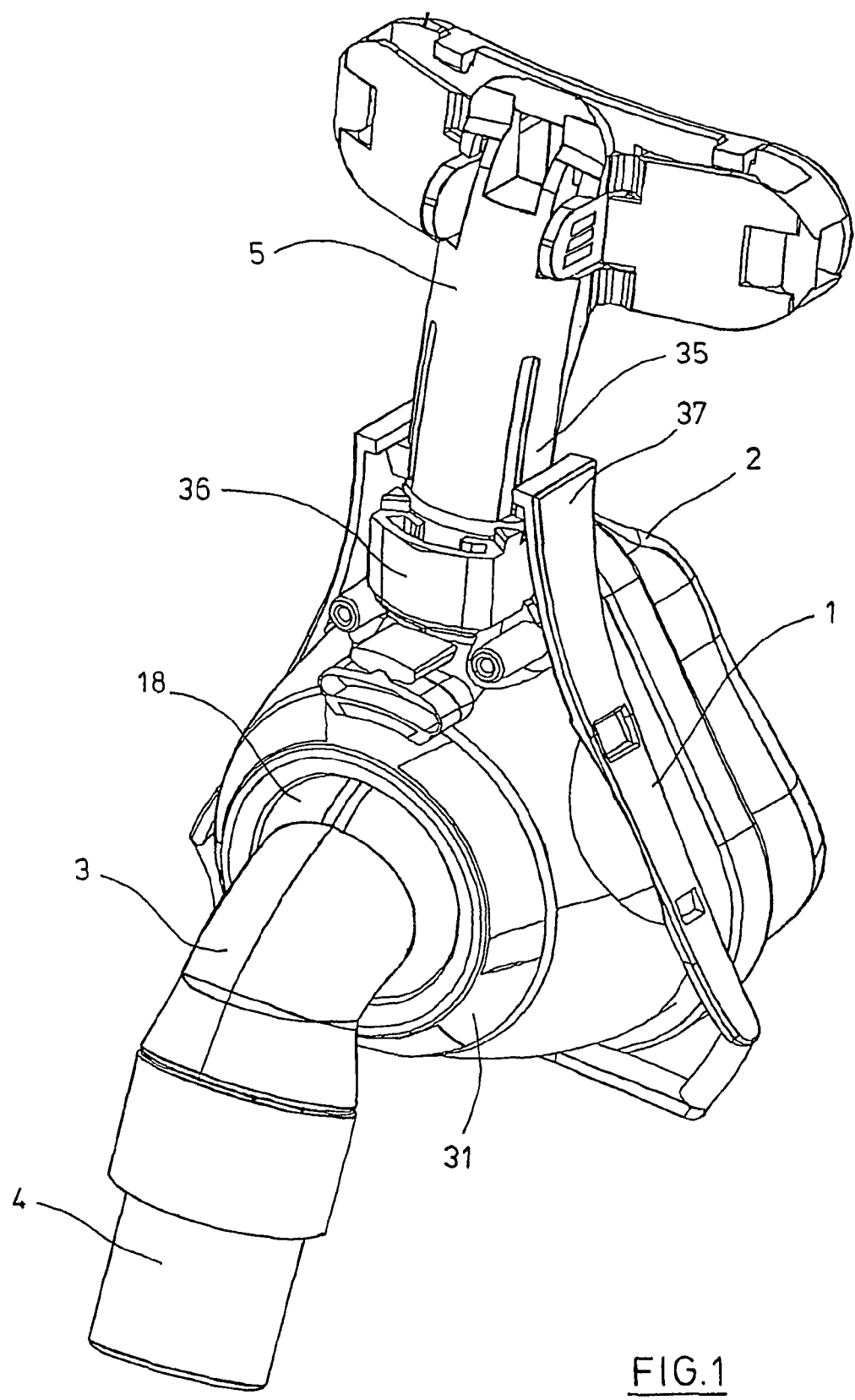
FIG. 1 shows a perspective view of a respiratory mask designed as a nasal mask.

FIG. 1 shows a respiratory mask that is designed as a nasal mask. The body 1 of the mask is made of a relatively strong material. The mask has a protruding edge 2, which rests against the face of a patient (not shown) and provides the necessary seal. An angled connector 3 connects the body 1 of the mask with a rotatably supported sleeve 4, which is used to attach a respiratory gas hose (not shown). To guarantee secure positioning of the respiratory mask on the patient's head, a forehead support 5 is used. The connector 3 and the mask body 1 are connected with each other by a ball-and-socket joint 18.

Figure 2:
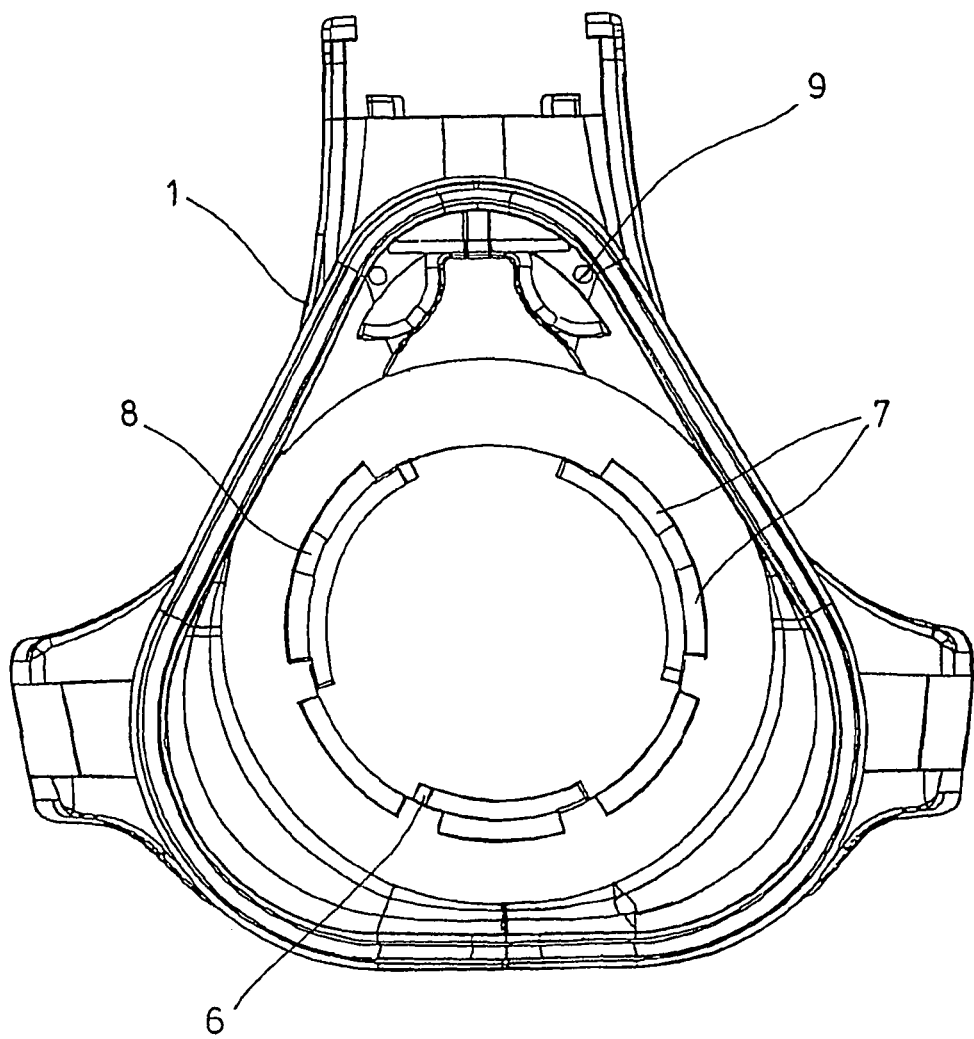
FIG. 2 shows a view of the inside of the mask, as seen from the rear of FIG. 1.

FIG. 2 shows the interior of the nasal mask from FIG. 1 in a direction of view from the inside towards a receptacle for the ball-and-socket joint 18, which is not shown in this drawing. Two pressure measurement connectors 9 are located in the upper area. Flow openings 7 lead to exhalation gaps 14 (not shown in this drawing). The flow openings 7 are bounded by flow guide structures 8, which are designed in such a way that they cause the respiratory gas flow to converge and to be guided into the exhalation gaps 14. The flow guide structures 8 are preferably designed in such a way that the respiratory gas flow is guided in funnel-like fashion into the exhalation gaps 14. The flow guide structures 8 in the upper region block the flow of respiratory gas in the direction of the patient's eyes. Inclined surfaces 6 are provided to facilitate the insertion of bayonet teeth 26 of a ball cage 24, which is not shown in this drawing.

Figure 3:
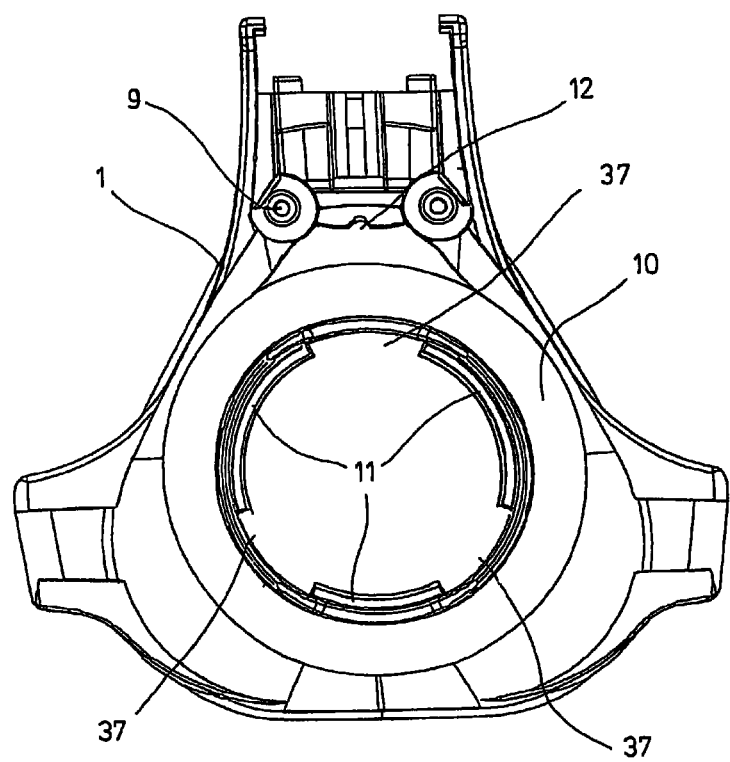
FIG. 3 shows a view of the outside of the mask, as seen from the front of FIG. 1.

FIG. 3 shows the view of the outside of the mask from FIG. 1, as seen from the front of the mask. An outflow surface 10 is formed as a ring. A retaining ring 31, which is not shown in this drawing, can be mounted and locked in place with the aid of ribs 11 and a catch 12.

Figure 4:
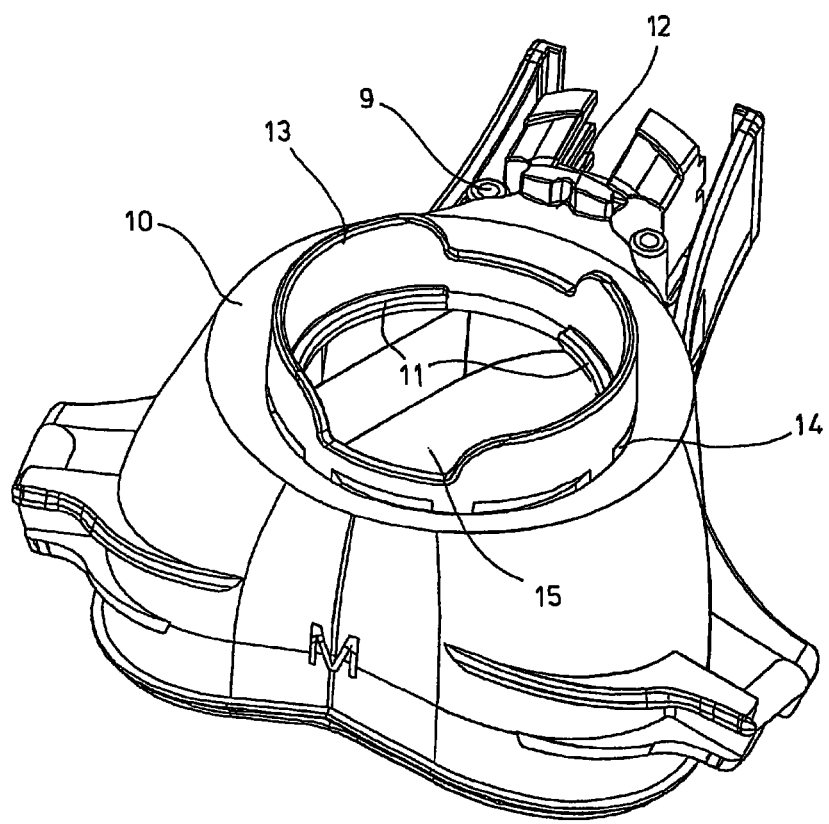
FIG. 4 shows a perspective view of the body of the mask in FIG. 1.

FIG. 4 shows a perspective view of the body of the nasal mask. A centering ring 13 is provided for mounting the retaining ring. Exhalation gaps 14 are located on the sides of the centering ring 13 and open towards the outflow surface 10. The centering ring 13 has recesses 15 that act as a mechanical coding system to prevent incorrect mounting of the retaining ring.

Figure 5:
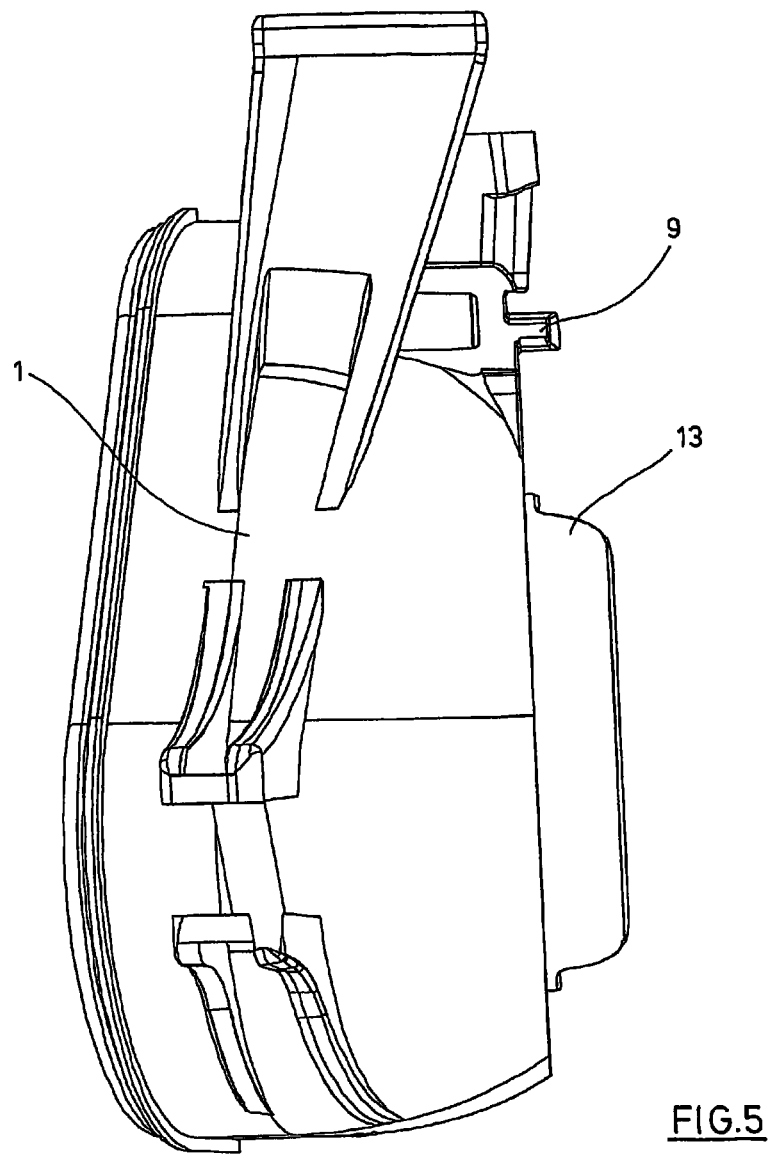
FIG. 5 shows a side view of the body of the mask.

FIG. 5 shows a side view of the body of the mask. The mask body 1, the centering ring 13, and the catch 12 are especially apparent in this view.

Figure 6:
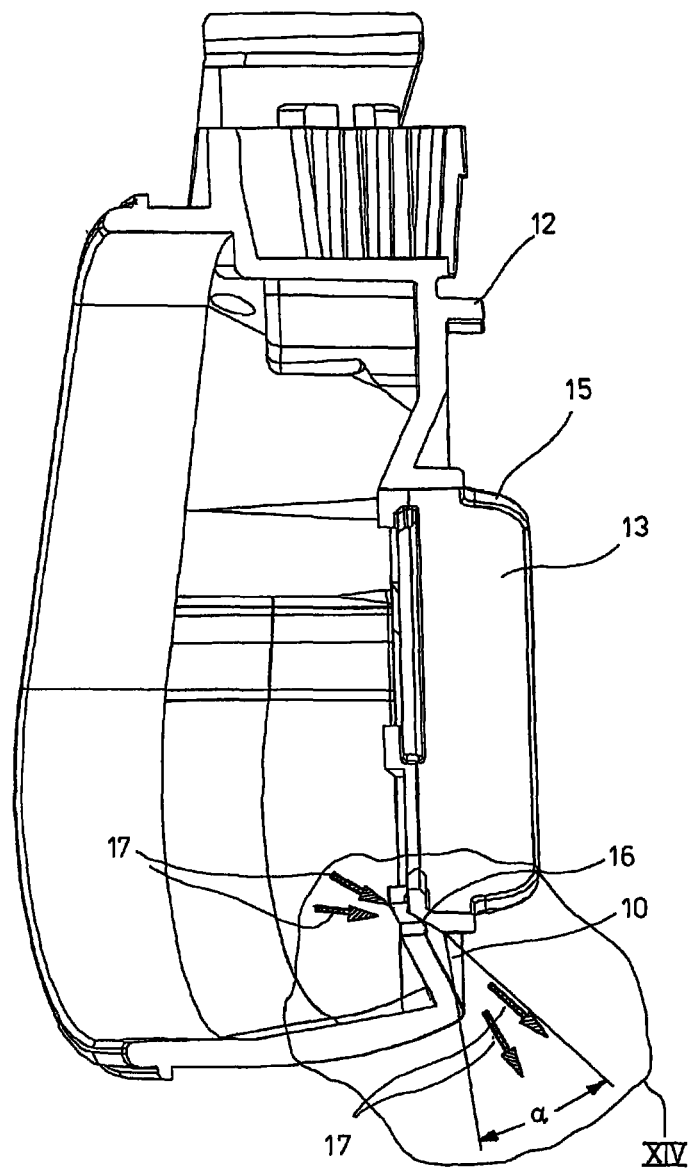
FIG. 6 shows a cross section through the plane of symmetry of the body of the mask.

FIG. 6 shows a cross section through the body of the mask from FIG. 5. The respiratory gas flow 17 moves along the flow guide structure 8 and into the exhalation gap 14. The flow guide structure 8 is preferably designed in such a way that the respiratory gas flow is guided in funnel-like fashion into the exhalation gap 14. The exhalation gap is bounded by the flow guide surface 16. In the exhalation gap, the respiratory gas flow is deflected at least once on the flow guide surface 16. Deflection of the respiratory gas flow can take place only in the exhalation gap 14, only in the area of transition of the mask body 1 into the exhalation gap 14, or combined in both areas.

The respiratory gas flow moves from inside the respiratory mask to outside the mask along the flow guide surface 16. After leaving the exhalation gap 14, which is the narrowest point, the respiratory gas flow leaves the respiratory mask in a fan-shaped flow path along the extended outflow surface 10. In this regard, the respiratory gas flow leaves the exhalation gap 14 at an angle alpha, which is preferably 10-45° to the vertical in FIG. 6. This vertical plane coincides with a plane that runs frontally to the face of a patient (not shown here).

Figure 7:
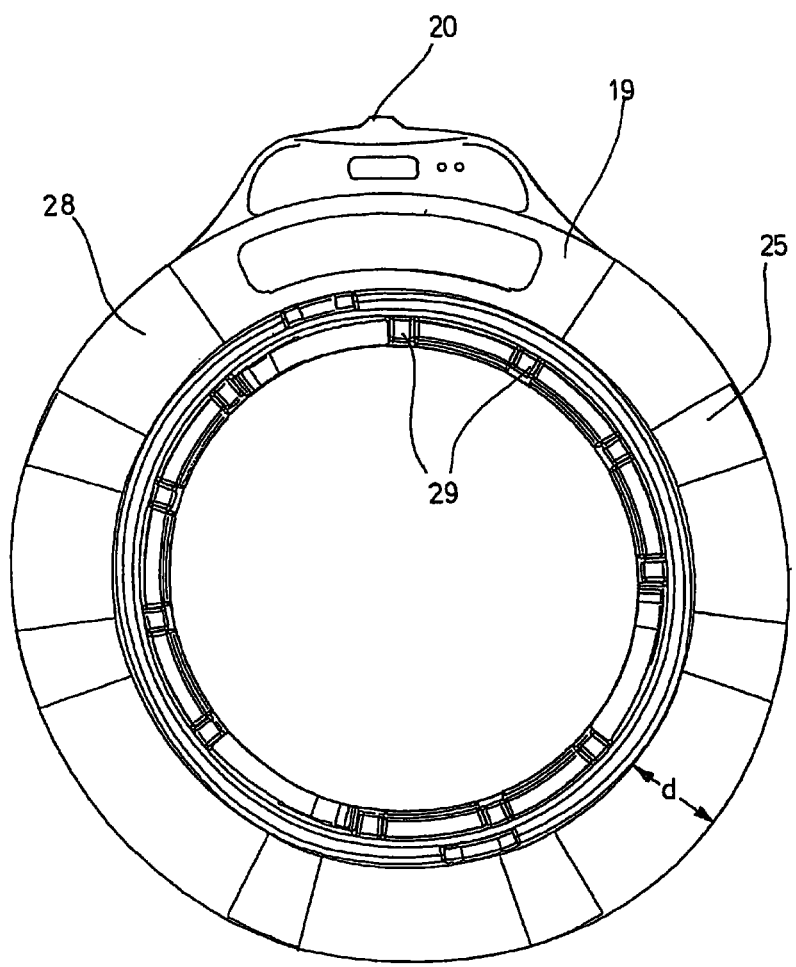
FIG. 7 shows a view of the retaining ring from the rear.

FIG. 7 shows a top view of a retaining ring 31 from the rear. It has a width d of less than 7 mm, as indicated by a double arrow. Spacer ribs 25 allow the retaining ring 31 to be mounted on the mask body 1 in the vicinity of the outflow surface 10 without play and with pretension. In the assembled state, the exhalation gap 14 is bounded by outflow surfaces 28 on the retaining ring 31 and the outflow surface 10 on the body 1 of the mask. A tab 20 on the retaining ring 31 is the complement to the catch 12 on the body 1 of the mask, so that additional securing of the retaining ring 31 on the body 1 of the mask is ensured. A surface segment 19 that rests on the outflow surface 10 in the assembled state guarantees that no air can flow off in the direction of the patient's eyes. Slots 29 between the elements of the ball cage 24 allow easy assembly.

Figure 8:
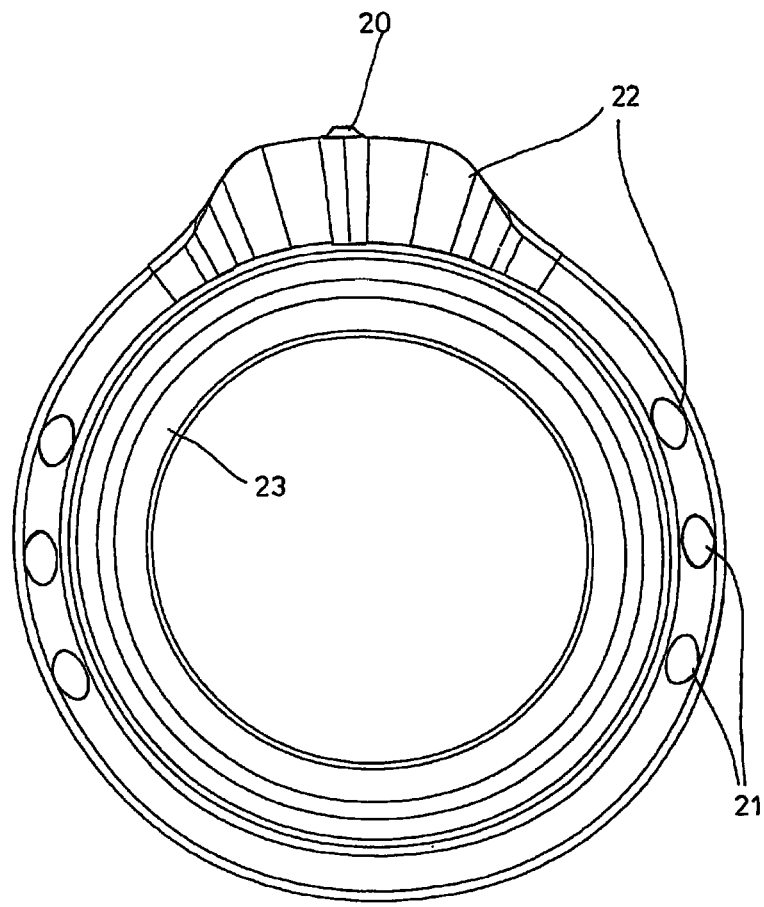
FIG. 8 shows a view of the retaining ring from the front.

FIG. 8 shows a view of the retaining ring 31 from the front. The inner region of the retaining ring 31 is made of a hard material 23, and the outer region is made of a soft material 22. Nubs 21 improve the grip.

Figure 9:
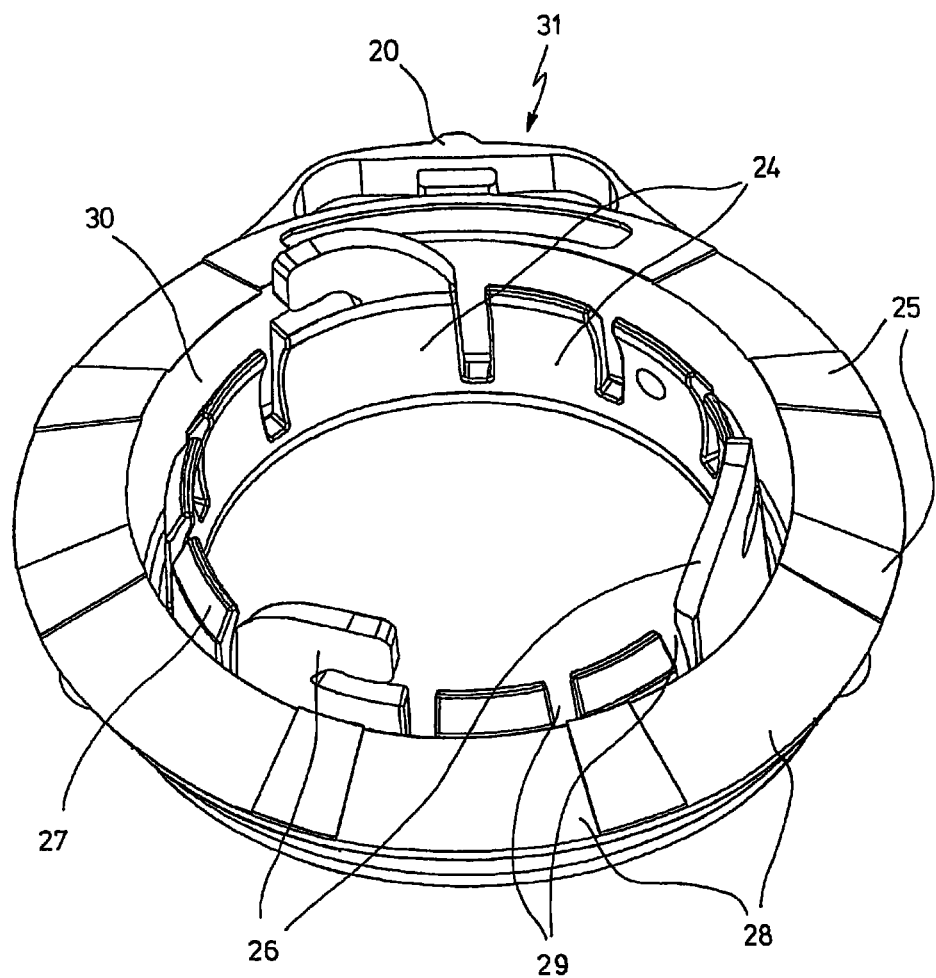
FIG. 9 shows a perspective view of the retaining ring.

FIG. 9 shows the retaining ring 31 in a rear perspective view. This viewing direction reveals the receptacle 30 for the web of the centering ring 13.

Figure 10:
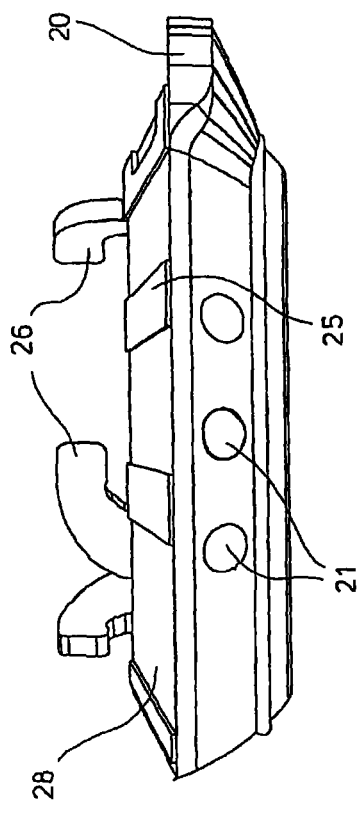
FIG. 10 shows a side view of the retaining ring.

FIG. 10 shows a side view of the retaining ring 31 and provides a view of the bayonet teeth 26.

Figure 11:
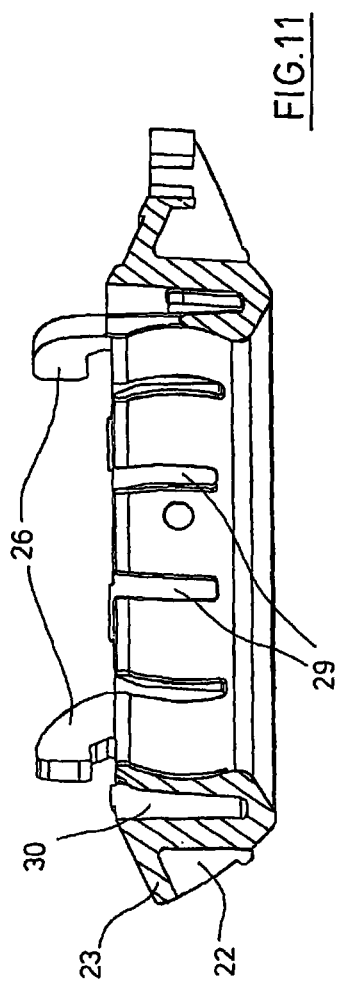
FIG. 11 shows a cross-sectional view of the retaining ring from FIG. 10.

FIG. 11 shows a cross-sectional view of the retaining ring 31 from FIG. 10.

The functions of the individual components illustrated in FIG. 9 to FIG. 11 will be explained again in detail later in connection with a description of the assembly and disassembly of the individual components for the specific purpose of further clarifying the mechanical significance and functionality of the individual components.

Figure 12:
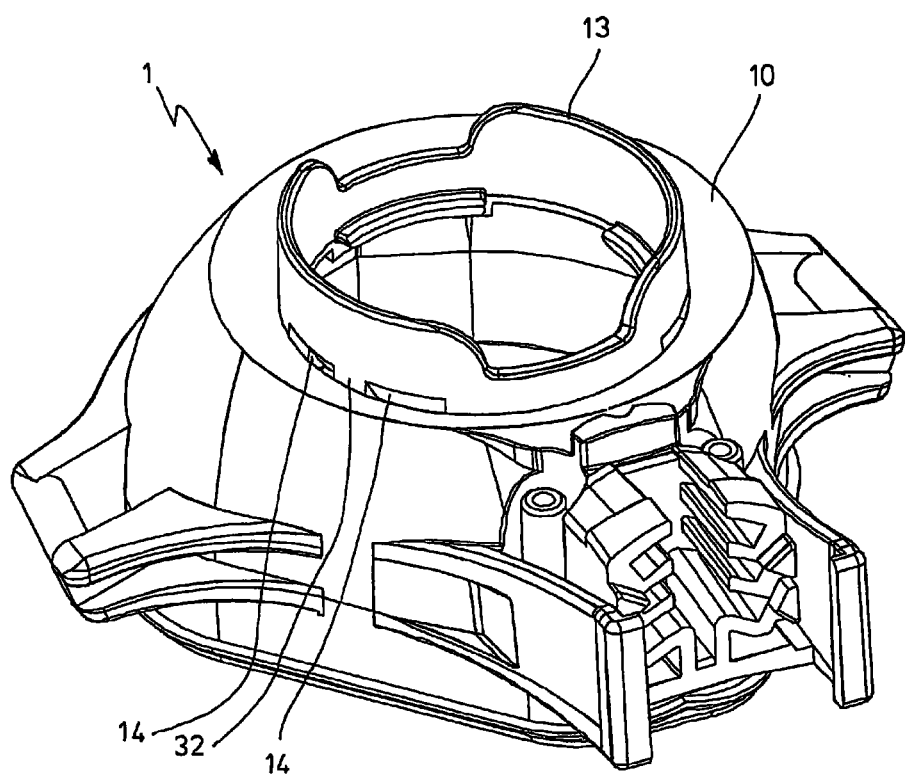
FIG. 12 shows a perspective view of the body of the mask.

The perspective view in FIG. 12 again illustrates the mask body 1 after removal of the forehead support 5, which is not shown in FIG. 12. In the transition region between the outflow surface 10 and the centering ring 13, especially the location of the exhalation gap 14 is once again evident. The exhalation gaps 14 have essentially rectangular cross-sectional shapes, and their longitudinal axes extend in the circumferential direction of the outflow surface 10. The individual exhalation gaps 14 are separated from each other by spacing elements 32. The spacing elements 32 bring about a mechanical connection between the centering ring 13 and the other material of the body 1 of the mask.

The exhalation gaps 14 are preferably arranged in such a way that they extend in a region of the centering ring 13 that faces the outflow surface 10. In this way, the respiratory gas emerging from the exhalation gaps 14 is guided directly into the area of the outflow surface 10. After leaving the exhalation gaps 14, the respiratory gas flow is deflected on the wide and extended outflow surfaces 10, 28 and flows diffusely and quietly into the surrounding environment through the outflow channel defined by the outflow surfaces.

Figure 13:
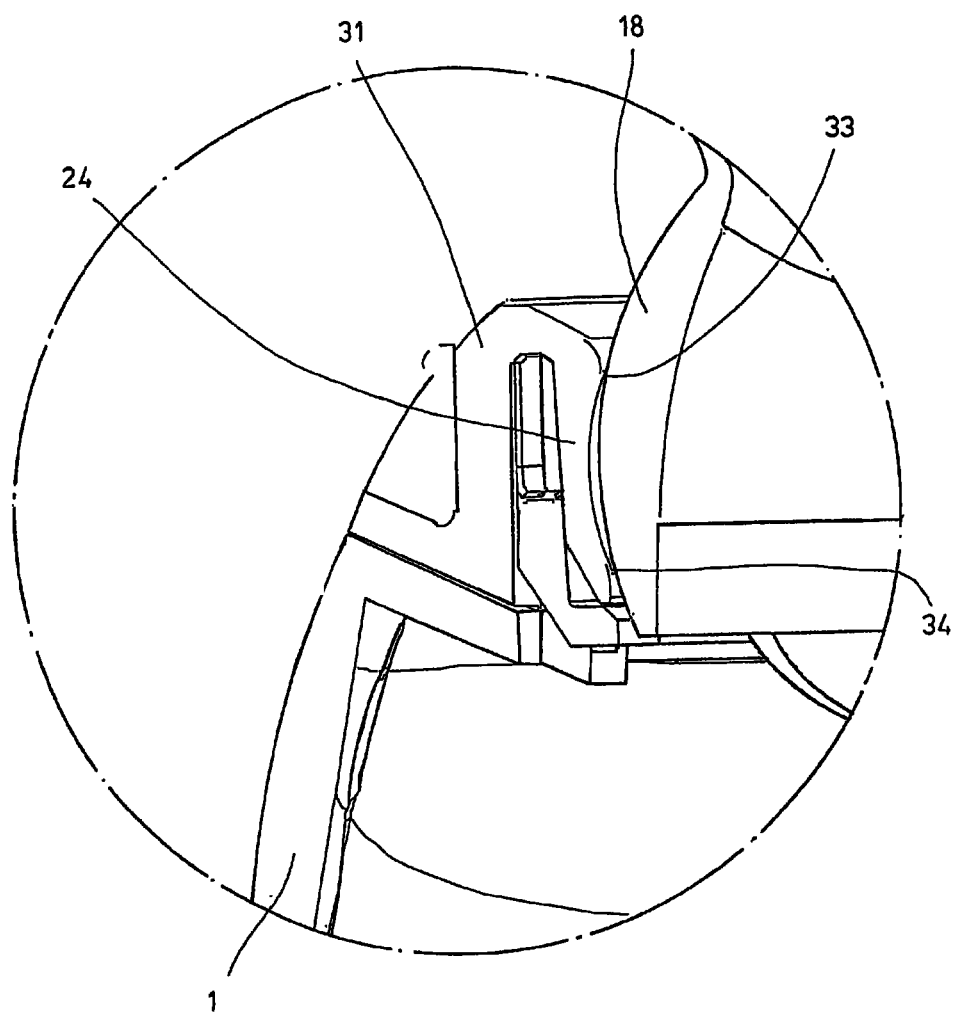
FIG. 13 shows a partial view of an enlarged cross section through the body of the mask in the vicinity of the ball-and-socket joint.

FIG. 13 shows an enlarged partial cross-sectional view in the area of transition between the ball-and-socket joint 18 and the retaining ring 31 held by the mask body 1. An arched course of the ball cage 24 is especially evident. The ball cage 24 extends concavely with a stronger curvature than a convexly shaped outer surface of the ball-and-socket joint 18. In this way, the ball-and-socket joint 18 is acted upon only along two guide lines, guide points 33, 34, or along linear segments of the ball cage 24. This makes it possible to compensate any production tolerances that may be present in the vicinity of the surfaces of the ball-and-socket joint 18 and/or the ball cage 24, since there is no surface guidance of the components on each other. Spring tensioning of the ball-and-socket joint 18 inside the ball cage 24 is preferably provided, so that secure support of the ball-and-socket joint 18 along the guide lines 33, 34 is guaranteed.

Figure 14:
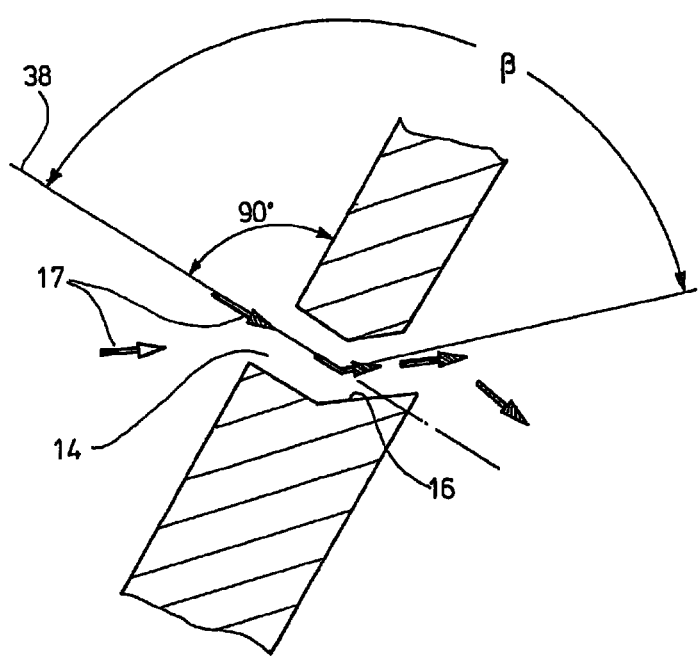
FIG. 14 shows an enlarged view of the detail XIV in FIG. 13.

FIG. 14 shows an enlarged section of the passage of the respiratory gas flow through the exhalation gap 14 along the flow guide surface 16 to the surrounding environment see FIG. 6. The respiratory gas flow 17 enters the exhalation gap 14, for example, in funnel-like fashion. The exhalation gap is bounded by the flow guide surface 16. In the exhalation gap, the respiratory gas flow is deflected at least once on the flow guide surface 16. The respiratory gas flow is guided from the inside of the respiratory mask to the outside along the flow guide surface 16. During the passage of the respiratory gas flow through the exhalation gap 14 along the flow guide surface 16 to the surrounding environment, the respiratory gas flow is deflected at an angle beta (β), which is preferably arranged 1-15° to a vertical line 38. This vertical line stands essentially at an angle of 90° perpendicularly to the plane formed by the parts of the body of the mask that bound the exhalation gap. During the passage of the respiratory gas flow through the exhalation gap 14 along the flow guide surface 16 to the surrounding environment, it is especially preferred for the respiratory gas flow to be deflected at an angle beta (β) arranged 2-7° to a vertical line 38.

To provide further explanation of the function of the individual components, we shall now explain the assembly of the individual parts, starting from their unassembled state. This assembly can also be easily managed by the patient himself. In a first step, the mask body 1, which is made of the harder material, and the protruding edge 2 of the mask are fitted together. To this end, the protruding edge 2 of the mask has a U-shaped profile that is not evident in the drawings. This U-shaped profile is pushed onto an edge of the body 1 of the mask. In the area of the point of contact between the protruding edge of the mask and the body of the mask, there is at least one undercut and at least one projection complementary to the undercut. The undercut is preferably located in the area of the softer component. The interaction of the undercut and projection in the assembled state provides a secure connection.

In the next assembly step, for example, a shaft 35 of the forehead support 2 can be inserted in a mounting support 36 of the mask body 1 and secured by means of at least one fastening device 37. However, the assembly of the forehead support 5 can also be carried out at any other desired point of the assembly operation.

In another assembly step, the retaining ring 31 is pushed onto the connector 3, starting from the sleeve 4, and is positioned in the area of the ball-and-socket joint 18. As the retaining ring 31 is being pushed onto the connector 3, it has an orientation such that, after the placement operation has been completed, the bayonet teeth 26 point in the direction away from the sleeve 4, and the ball-and-socket joint 18 is partially enclosed by the ball cage 24 of the retaining ring 31.

In a final assembly step, the retaining ring 31 is positioned, together with the connector 3, in the vicinity of the centering ring 13 of the body 1 of the mask. Due to the asymmetrical arrangement of the ribs 11 along the periphery, as shown, for example, in FIG. 3, and the corresponding arrangement of the bayonet teeth 26, the bayonet teeth 26 can be inserted in the recesses 37 between the ribs 11 only in a single predetermined position. This creates a mechanical coding system.

After the bayonet teeth 26 have been inserted in the recesses 37 between the ribs 11, the retaining ring 31 is twisted relative to the body 1 of the mask in such a way that the catch 12 is engaged. The catch 12 is preferably designed as a projection of the retaining ring 31 that engages a corresponding recess in the mask body 1. In principle, however, the device can also be constructed in the opposite way. Elastic engagement of the catch 12 is assisted if the retaining ring 31 is made of a relatively soft material, so that the likewise soft projection of the retaining ring 31 can be inserted in the recess of the mask body 1 and can also be twisted back out again.

After the retaining ring 31 has been twisted relative to the mask body 1, the assembly operation is complete. The final position of the retaining ring 31 is predetermined by a lateral stop of the bayonet teeth 26 on the ribs 11. In addition, the bayonet teeth 26 engage behind the ribs 11, so that the total unit is also able to withstand tensile loads. The respiratory mask is disassembled in the reverse order of assembly described above.

As a result of the design of the retaining ring 31, it can be mounted on the mask body 1 without play and, if necessary, with pretensioning. Consequently, the width of the exhalation gap or gaps 14 now depends only on the tolerance of the height of the spacer ribs 25. The exhalation gap 14 is thus realized in a way that is extremely uniform and largely independent of tolerance. This in turn means that the discharge of the respiratory gas through the exhalation gap 14 is extremely constant and thus that the sound emissions produced by this discharge are likewise extremely constant.

The design of the retaining ring 31 allows the ball-and-socket joint 18 to be inserted in the elastic ball cage 24 of the retaining ring 31 and allows the ball cage 24 to enclose the ball-and-socket joint 18 at least partially. The ball-and-socket joint 18 is secured in the ball cage 24 by inserting the centering ring 13 in the receptacle 30 present in the retaining ring 31. As a result, the elastic elements of the ball cage 24 are bounded on one side by the ball-and-socket joint 18 and on the other side by the centering ring 13. In the assembled state, the ball-and-socket joint is secured in the area of the mask in this way. The mobility of the ball-and-socket joint, on the one hand, and the seal relative to the respiratory gas in the area between the ball-and-socket joint and the ball cage, on the other hand, are determined by the exact dimensioning and narrow tolerances.

The invention claimed is:

1. A respiratory mask comprising a mask body and at least one ball-and-socket joint which is at least partially enclosed on the outside by a ball cage, wherein the ball-and-socket joint is secured in the ball cage by a centering ring by inserting the centering ring in a receptacle in a retaining ring, which centering ring rests against at least certain outside areas of the ball cage, and wherein at least one catch is provided for locking the retaining ring relative to the body of the mask, whereby in an assembled state the ball-and-socket joint is fixed in an area of the mask, the centering ring being part of the mask body and the receptacle and the ball cage being part of the retaining ring.

2. A respiratory mask comprising a mask body and at least one ball-and-socket joint which is at least partially enclosed on the outside by a ball cage, wherein the ball-and-socket joint in the ball cage rests permanently on fewer than four points, wherein the ball-and-socket joint is secured in the ball cage by a centering ring by inserting the centering ring in a receptacle in a retaining ring, and wherein at least one catch is provided for locking the retaining ring relative to the body of the mask, whereby in an assembled state the ball-and-socket joint is fixed in an area of the mask, the centering ring being part of the mask body and the receptacle and the ball cage being part of the retaining ring.

3. A respiratory mask comprising a mask body and at least one ball-and-socket joint which is at least partially enclosed on the outside by a ball cage, wherein the ball cage extends concavely with a stronger curvature than a convexly shaped outer surface of the ball-and-socket joint, wherein the ball-and-socket joint is secured in the ball cage by a centering ring by inserting the centering ring in a receptacle in a retaining ring, and wherein at least one catch is provided for locking the retaining ring relative to the body of the mask, whereby in an assembled state the ball-and-socket joint is fixed in an area of the mask, the centering ring being part of the mask body and the receptacle and the ball cage being part of the retaining ring.

* * * * *